(12) United States Patent
Rieping

(10) Patent No.: US 6,623,944 B2
(45) Date of Patent: Sep. 23, 2003

(54) PROCESS FOR PREPARATION OF D-PANTOTHENIC ACID AND/OR SALTS THEREOF

(75) Inventor: Mechthild Rieping, Bielefeld (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/096,571

(22) Filed: Mar. 14, 2002

(65) Prior Publication Data
US 2002/0173010 A1 Nov. 21, 2002

Related U.S. Application Data
(60) Provisional application No. 60/304,776, filed on Jul. 13, 2001.

(30) Foreign Application Priority Data
Mar. 14, 2001 (DE) .......................... 101 12 102

(51) Int. Cl.[7] .............................. C12P 7/42; C12P 9/04; C12N 1/20; C12N 15/00; C07H 21/04; A23L 1/00
(52) U.S. Cl. .................. 435/146; 435/190; 435/252.33; 435/320.1; 536/232; 426/7
(58) Field of Search .................. 435/146, 190, 435/252.33, 320.1; 536/23.2; 426/7

(56) References Cited

U.S. PATENT DOCUMENTS

| 4,278,765 A | 7/1981 | Debabov et al. |
| 5,518,906 A | 5/1996 | Hikichi et al. |

FOREIGN PATENT DOCUMENTS

| EP | 0 493 060 | 7/1992 |
| EP | 0 590 857 | 4/1994 |
| EP | 1 001 027 | 5/2000 |
| EP | 1 006 193 | 6/2000 |
| EP | 1 050 219 | 11/2000 |
| WO | WO96/33283 | 10/1996 |
| WO | WO97/10340 | 3/1997 |
| WO | WO 02/29020 | 4/2002 |
| WO | WO 02 36797 | 5/2002 |

OTHER PUBLICATIONS

XP–000987282 "Molecular Cloning of the Gene (poxB) Encoding the Pyruvate Oxidase of *Escherichia coli*, a Lipid–Activated Enzyme" Journal of Bacteriology, Washington, D.C., vol. 160, No. 3, Dec. 1984, pp. 1088–1092.
C. Grabau, et al. Nucleic Acids Research. vol. 14, No. 13, pp. 5449–5460 (1986).
Blatter et al., Science vol. 277 pp. 1453–1462, (1997) Accession No. AE000188.
Jenson et al., Biotechnology and Bioengineering 58: pp. 191–195 (1998).
Carrier and Keasling (Biotechnology Progress 15, 58–64 (1999).
Franch and Gerdes (Current Opinion in Microbiology 3, 159–164 (2000).
Z. Qiu, et al. Journal of Biological Chemistry, vol. 272, No. 13, Issue of Mar. 28, :pp. 8611–8617 (1997).
Yano et al. (Proceedings of the National Academy of Sciences, USA 95, 5511–5515 (1998).
Wente and Schachmann (Journal of Biological Chemistry, vol. 266, No. 31, pp. 20833–20839 (1991).

(List continued on next page.)

Primary Examiner—Rebecca E. Prouty
Assistant Examiner—Sheridan L Swope
(74) Attorney, Agent, or Firm—Oblon, Spivak, McClelland, Maier & Neustadt, P.C.

(57) ABSTRACT

D-pantothenic acid and/or a salt thereof or feedstuffs additives comprising these are prepared by fermentation of a microorganism of the Enterobacteriaceae family, in particular one which already produces D-pantothenic acid, wherein the nucleotide sequence(s) in the microorganism which code(s) for the poxB gene is (are) attenuated, in particular eliminated.

9 Claims, 3 Drawing Sheets

OTHER PUBLICATIONS

Hamilton et al. (Journal of Bacteriology, vol. 171, No. 9, pp. 4617–4622 (1989).

Martinez–Morales et al. (Journal of Bacteriology, vol. 181, No. 22, pp. 7143–7148 (1999).

Boyd et al. (Journal of Bacteriology, vol. 182, No. 3, pp. 842–847 (2000).

Duncan and Coggins, Biochemical Journal, vol. 234, pp. 49–57 (1986).

Okamura–Ikeda et al., European Journal of Biochemistry, vol. 216, pp. 539–548 (1993).

Medina et al., Journal of Bacteriology, vol. 172, No. 12, pp. 7151–7156 (1990).

Velisek; Chromatographic Science, vol. 60, pp. 515–560 (1992).

Chung et al. (Proceedings of the National Academy of Sciences of the United States of America USA, vol. 86, pp. 2172–2175 (1989).-

SEQUENCE LISTING

<160> NUMBER OF SEQ ID NOS: 14

<210> SEQ ID NO 1
<211> LENGTH: 1719
<212> TYPE: DNA
<213> ORGANISM: Escherichia coli
<220> FEATURE:
<221> NAME/KEY: CDS
<222> LOCATION: (1)..(1716)
<223> OTHER INFORMATION:

<400> SEQUENCE: 1

```
atg aaa caa acg gtt gca gct tat atc gcc aaa aca ctc gaa tcg gca      48
Met Lys Gln Thr Val Ala Ala Tyr Ile Ala Lys Thr Leu Glu Ser Ala
1               5                   10                  15 ggg gtg aaa cgc atc tgg gga gtc aca ggc gac tct ctg aac ggt ctt      96
Gly Val Lys Arg Ile Trp Gly Val Thr Gly Asp Ser Leu Asn Gly Leu
```

-continued

| | | | | | | | | | | | | | | | | |
|---|---|---|---|---|---|---|---|---|---|---|---|---|---|---|---|---|
| | | 20 | | | | 25 | | | | 30 | | | | | | |
| agt | gac | agt | ctt | aat | cgc | atg | ggc | acc | atc | gag | tgg | atg | tcc | acc | cgc | 144 |
| Ser | Asp | Ser | Leu | Asn | Arg | Met | Gly | Thr | Ile | Glu | Trp | Met | Ser | Thr | Arg | |
| | | 35 | | | | 40 | | | | 45 | | | | | | |
| cac | gaa | gaa | gtg | gcg | gcc | ttt | gcc | gct | ggc | gct | gaa | gca | caa | ctt | agc | 192 |
| His | Glu | Glu | Val | Ala | Ala | Phe | Ala | Ala | Gly | Ala | Glu | Ala | Gln | Leu | Ser | |
| | 50 | | | | | 55 | | | | 60 | | | | | | |
| gga | gaa | ctg | gcg | gtc | tgc | gcc | gga | tcg | tgc | ggc | ccc | ggc | aac | ctg | cac | 240 |
| Gly | Glu | Leu | Ala | Val | Cys | Ala | Gly | Ser | Cys | Gly | Pro | Gly | Asn | Leu | His | |
| 65 | | | | | 70 | | | | | 75 | | | | | 80 | |
| tta | atc | aac | ggc | ctg | ttc | gat | tgc | cac | cgc | aat | cac | gtt | ccg | gta | ctg | 288 |
| Leu | Ile | Asn | Gly | Leu | Phe | Asp | Cys | His | Arg | Asn | His | Val | Pro | Val | Leu | |
| | | | | 85 | | | | | 90 | | | | | 95 | | |
| gcg | att | gcc | gct | cat | att | ccc | tcc | agc | gaa | att | ggc | agc | ggc | tat | ttc | 336 |
| Ala | Ile | Ala | Ala | His | Ile | Pro | Ser | Ser | Glu | Ile | Gly | Ser | Gly | Tyr | Phe | |
| | | | 100 | | | | | 105 | | | | | 110 | | | |
| cag | gaa | acc | cac | cca | caa | gag | cta | ttc | cgc | gaa | tgt | agt | cac | tat | tgc | 384 |
| Gln | Glu | Thr | His | Pro | Gln | Glu | Leu | Phe | Arg | Glu | Cys | Ser | His | Tyr | Cys | |
| | | | 115 | | | | | 120 | | | | | 125 | | | |
| gag | ctg | gtt | tcc | agc | ccg | gag | cag | atc | cca | caa | gta | ctg | gcg | att | gcc | 432 |
| Glu | Leu | Val | Ser | Ser | Pro | Glu | Gln | Ile | Pro | Gln | Val | Leu | Ala | Ile | Ala | |
| | 130 | | | | | 135 | | | | 140 | | | | | | |
| atg | cgc | aaa | gcg | gtg | ctt | aac | cgt | ggc | gtt | tcg | gtt | gtc | gtg | tta | cca | 480 |
| Met | Arg | Lys | Ala | Val | Leu | Asn | Arg | Gly | Val | Ser | Val | Val | Val | Leu | Pro | |
| 145 | | | | | 150 | | | | | 155 | | | | | 160 | |
| ggc | gac | gtg | gcg | tta | aaa | cct | gcg | cca | gaa | ggg | gca | acc | atg | cac | tgg | 528 |
| Gly | Asp | Val | Ala | Leu | Lys | Pro | Ala | Pro | Glu | Gly | Ala | Thr | Met | His | Trp | |
| | | | | 165 | | | | | 170 | | | | | 175 | | |
| tat | cat | gcg | cca | caa | cca | gtc | gtg | acg | ccg | gaa | gaa | gaa | gag | tta | cgc | 576 |
| Tyr | His | Ala | Pro | Gln | Pro | Val | Val | Thr | Pro | Glu | Glu | Glu | Glu | Leu | Arg | |
| | | | 180 | | | | | 185 | | | | | 190 | | | |
| aaa | ctg | gcg | caa | ctg | ctg | cgt | tat | tcc | agc | aat | atc | gcc | ctg | atg | tgt | 624 |
| Lys | Leu | Ala | Gln | Leu | Leu | Arg | Tyr | Ser | Ser | Asn | Ile | Ala | Leu | Met | Cys | |
| | | 195 | | | | | 200 | | | | | 205 | | | | |
| ggc | agc | ggc | tgc | gcg | ggg | gcg | cat | aaa | gag | tta | gtt | gag | ttt | gcc | ggg | 672 |
| Gly | Ser | Gly | Cys | Ala | Gly | Ala | His | Lys | Glu | Leu | Val | Glu | Phe | Ala | Gly | |
| | 210 | | | | | 215 | | | | 220 | | | | | | |
| aaa | att | aaa | gcg | cct | att | gtt | cat | gcc | ctg | cgc | ggt | aaa | gaa | cat | gtc | 720 |
| Lys | Ile | Lys | Ala | Pro | Ile | Val | His | Ala | Leu | Arg | Gly | Lys | Glu | His | Val | |
| 225 | | | | | 230 | | | | | 235 | | | | | 240 | |
| gaa | tac | gat | aat | ccg | tat | gat | gtt | gga | atg | acc | ggg | tta | atc | ggc | ttc | 768 |
| Glu | Tyr | Asp | Asn | Pro | Tyr | Asp | Val | Gly | Met | Thr | Gly | Leu | Ile | Gly | Phe | |
| | | | | 245 | | | | | 250 | | | | | 255 | | |
| tcg | tca | ggt | ttc | cat | acc | atg | atg | aac | gcc | gac | acg | tta | gtg | cta | ctc | 816 |
| Ser | Ser | Gly | Phe | His | Thr | Met | Met | Asn | Ala | Asp | Thr | Leu | Val | Leu | Leu | |
| | | | | 260 | | | | | 265 | | | | | 270 | | |
| ggc | acg | caa | ttt | ccc | tac | cgc | gcc | ttc | tac | ccg | acc | gat | gcc | aaa | atc | 864 |
| Gly | Thr | Gln | Phe | Pro | Tyr | Arg | Ala | Phe | Tyr | Pro | Thr | Asp | Ala | Lys | Ile | |
| | | 275 | | | | | 280 | | | | | 285 | | | | |
| att | cag | att | gat | atc | aac | cca | gcc | agc | atc | ggc | gct | cac | agc | aag | gtg | 912 |
| Ile | Gln | Ile | Asp | Ile | Asn | Pro | Ala | Ser | Ile | Gly | Ala | His | Ser | Lys | Val | |
| | | 290 | | | | | 295 | | | | | 300 | | | | |
| gat | atg | gca | ctg | gtc | ggc | gat | atc | aag | tcg | act | ctg | cgt | gca | ttg | ctt | 960 |
| Asp | Met | Ala | Leu | Val | Gly | Asp | Ile | Lys | Ser | Thr | Leu | Arg | Ala | Leu | Leu | |
| 305 | | | | | 310 | | | | | 315 | | | | | 320 | |
| cca | ttg | gtg | gaa | gaa | aaa | gcc | gat | cgc | aag | ttt | ctg | gat | aaa | gcg | ctg | 1008 |
| Pro | Leu | Val | Glu | Glu | Lys | Ala | Asp | Arg | Lys | Phe | Leu | Asp | Lys | Ala | Leu | |
| | | | | 325 | | | | | 330 | | | | | 335 | | |
| gaa | gat | tac | cgc | gac | gcc | cgc | aaa | ggg | ctg | gac | gat | tta | gct | aaa | ccg | 1056 |

```
Glu Asp Tyr Arg Asp Ala Arg Lys Gly Leu Asp Asp Leu Ala Lys Pro
            340                 345                 350 agc gag aaa gcc att cac ccg caa tat ctg gcg cag caa att agt cat    1104
Ser Glu Lys Ala Ile His Pro Gln Tyr Leu Ala Gln Gln Ile Ser His
        355                 360                 365 ttt gcc gcc gat gac gct att ttc acc tgt gac gtt ggt acg cca acg    1152
Phe Ala Ala Asp Asp Ala Ile Phe Thr Cys Asp Val Gly Thr Pro Thr
370                 375                 380 gtg tgg gcg gca cgt tat cta aaa atg aac ggc aag cgt cgc ctg tta    1200
Val Trp Ala Ala Arg Tyr Leu Lys Met Asn Gly Lys Arg Arg Leu Leu
385                 390                 395                 400 ggt tcg ttt aac cac ggt tcg atg gct aac gcc atg ccg cag gcg ctg    1248
Gly Ser Phe Asn His Gly Ser Met Ala Asn Ala Met Pro Gln Ala Leu
                405                 410                 415 ggt gcg cag gcg aca gag cca gaa cgt cag gtg gtc gcc atg tgc ggc    1296
Gly Ala Gln Ala Thr Glu Pro Glu Arg Gln Val Val Ala Met Cys Gly
            420                 425                 430 gat ggc ggt ttt agc atg ttg atg ggc gat ttc ctc tca gta gtg cag    1344
Asp Gly Gly Phe Ser Met Leu Met Gly Asp Phe Leu Ser Val Val Gln
        435                 440                 445 atg aaa ctg cca gtg aaa att gtc gtc ttt aac aac agc gtg ctg ggc    1392
Met Lys Leu Pro Val Lys Ile Val Val Phe Asn Asn Ser Val Leu Gly
450                 455                 460 ttt gtg gcg atg gag atg aaa gct ggt ggc tat ttg act gac ggc acc    1440
Phe Val Ala Met Glu Met Lys Ala Gly Gly Tyr Leu Thr Asp Gly Thr
465                 470                 475                 480 gaa cta cac gac aca aac ttt gcc cgc att gcc gaa gcg tgc ggc att    1488
Glu Leu His Asp Thr Asn Phe Ala Arg Ile Ala Glu Ala Cys Gly Ile
                485                 490                 495 acg ggt atc cgt gta gaa aaa gcg tct gaa gtt gat gaa gcc ctg caa    1536
Thr Gly Ile Arg Val Glu Lys Ala Ser Glu Val Asp Glu Ala Leu Gln
            500                 505                 510 cgc gcc ttc tcc atc gac ggt ccg gtg ttg gtg gat gtg gtg gtc gcc    1584
Arg Ala Phe Ser Ile Asp Gly Pro Val Leu Val Asp Val Val Val Ala
        515                 520                 525 aaa gaa gag tta gcc att cca ccg cag atc aaa ctc gaa cag gcc aaa    1632
Lys Glu Glu Leu Ala Ile Pro Pro Gln Ile Lys Leu Glu Gln Ala Lys
530                 535                 540 ggt ttc agc ctg tat atg ctg cgc gca atc atc agc gga cgc ggt gat    1680
Gly Phe Ser Leu Tyr Met Leu Arg Ala Ile Ile Ser Gly Arg Gly Asp
545                 550                 555                 560 gaa gtg atc gaa ctg gcg aaa aca aac tgg cta agg taa                1719
Glu Val Ile Glu Leu Ala Lys Thr Asn Trp Leu Arg
                565                 570

<210> SEQ ID NO 2
<211> LENGTH: 572
<212> TYPE: PRT
<213> ORGANISM: Escherichia coli

<400> SEQUENCE: 2

Met Lys Gln Thr Val Ala Ala Tyr Ile Ala Lys Thr Leu Glu Ser Ala
1               5                   10                  15

Gly Val Lys Arg Ile Trp Gly Val Thr Gly Asp Ser Leu Asn Gly Leu
            20                  25                  30

Ser Asp Ser Leu Asn Arg Met Gly Thr Ile Glu Trp Met Ser Thr Arg
        35                  40                  45

His Glu Glu Val Ala Ala Phe Ala Ala Gly Ala Glu Ala Gln Leu Ser
    50                  55                  60
```

```
Gly Glu Leu Ala Val Cys Ala Gly Ser Cys Gly Pro Gly Asn Leu His
 65                  70                  75                  80

Leu Ile Asn Gly Leu Phe Asp Cys His Arg Asn His Val Pro Val Leu
                 85                  90                  95

Ala Ile Ala Ala His Ile Pro Ser Ser Glu Ile Gly Ser Gly Tyr Phe
                100                 105                 110

Gln Glu Thr His Pro Gln Glu Leu Phe Arg Glu Cys Ser His Tyr Cys
            115                 120                 125

Glu Leu Val Ser Ser Pro Glu Gln Ile Pro Gln Val Leu Ala Ile Ala
        130                 135                 140

Met Arg Lys Ala Val Leu Asn Arg Gly Val Ser Val Val Leu Pro
145                 150                 155                 160

Gly Asp Val Ala Leu Lys Pro Ala Pro Glu Gly Ala Thr Met His Trp
                165                 170                 175

Tyr His Ala Pro Gln Pro Val Val Thr Pro Glu Glu Glu Leu Arg
                180                 185                 190

Lys Leu Ala Gln Leu Leu Arg Tyr Ser Ser Asn Ile Ala Leu Met Cys
                195                 200                 205

Gly Ser Gly Cys Ala Gly Ala His Lys Glu Leu Val Glu Phe Ala Gly
            210                 215                 220

Lys Ile Lys Ala Pro Ile Val His Ala Leu Arg Gly Lys Glu His Val
225                 230                 235                 240

Glu Tyr Asp Asn Pro Tyr Asp Val Gly Met Thr Gly Leu Ile Gly Phe
                245                 250                 255

Ser Ser Gly Phe His Thr Met Met Asn Ala Asp Thr Leu Val Leu Leu
            260                 265                 270

Gly Thr Gln Phe Pro Tyr Arg Ala Phe Tyr Pro Thr Asp Ala Lys Ile
        275                 280                 285

Ile Gln Ile Asp Ile Asn Pro Ala Ser Ile Gly Ala His Ser Lys Val
        290                 295                 300

Asp Met Ala Leu Val Gly Asp Ile Lys Ser Thr Leu Arg Ala Leu Leu
305                 310                 315                 320

Pro Leu Val Glu Glu Lys Ala Asp Arg Lys Phe Leu Asp Lys Ala Leu
                325                 330                 335

Glu Asp Tyr Arg Asp Ala Arg Lys Gly Leu Asp Asp Leu Ala Lys Pro
                340                 345                 350

Ser Glu Lys Ala Ile His Pro Gln Tyr Leu Ala Gln Gln Ile Ser His
            355                 360                 365

Phe Ala Ala Asp Asp Ala Ile Phe Thr Cys Asp Val Gly Thr Pro Thr
        370                 375                 380

Val Trp Ala Ala Arg Tyr Leu Lys Met Asn Gly Lys Arg Arg Leu Leu
385                 390                 395                 400

Gly Ser Phe Asn His Gly Ser Met Ala Asn Ala Met Pro Gln Ala Leu
                405                 410                 415

Gly Ala Gln Ala Thr Glu Pro Glu Arg Gln Val Val Ala Met Cys Gly
            420                 425                 430

Asp Gly Gly Phe Ser Met Leu Met Gly Asp Phe Leu Ser Val Val Gln
        435                 440                 445

Met Lys Leu Pro Val Lys Ile Val Phe Asn Asn Ser Val Leu Gly
            450                 455                 460

Phe Val Ala Met Glu Met Lys Ala Gly Gly Tyr Leu Thr Asp Gly Thr
465                 470                 475                 480

Glu Leu His Asp Thr Asn Phe Ala Arg Ile Ala Glu Ala Cys Gly Ile
```

```
                    485                 490                 495
Thr Gly Ile Arg Val Glu Lys Ala Ser Glu Val Asp Glu Ala Leu Gln
                500                 505                 510

Arg Ala Phe Ser Ile Asp Gly Pro Val Leu Val Asp Val Val Ala
            515                 520                 525

Lys Glu Glu Leu Ala Ile Pro Pro Gln Ile Lys Leu Glu Gln Ala Lys
        530                 535                 540

Gly Phe Ser Leu Tyr Met Leu Arg Ala Ile Ile Ser Gly Arg Gly Asp
545                 550                 555                 560

Glu Val Ile Glu Leu Ala Lys Thr Asn Trp Leu Arg
                565                 570
```

```
<210> SEQ ID NO 3
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
ctgaacggtc ttagtgacag                                           20

<210> SEQ ID NO 4
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
aggcctggaa taacgcagca gttg                                      24

<210> SEQ ID NO 5
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
ctgcgtgcat tgcttccatt g                                         21

<210> SEQ ID NO 6
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
gccagttcga tcacttcatc ac                                        22

<210> SEQ ID NO 7
<211> LENGTH: 1454
<212> TYPE: DNA
<213> ORGANISM: Escherichia coli
<220> FEATURE:
<221> NAME/KEY: misc_feature
<222> LOCATION: (1)..(1454)
<223> OTHER INFORMATION: Mutagene DNA
<221> NAME/KEY: misc_feature
<222> LOCATION: (1)..(56)
<223> OTHER INFORMATION: Technical-grade DNA/Residues of polylinker
      sequence
<221> NAME/KEY: misc_feature
```

```
<222> LOCATION: (57)..(577)
<223> OTHER INFORMATION: Part of the 5' region (poxB1) of the poxB gene
<221> NAME/KEY: misc_feature
<222> LOCATION: (578)..(646)
<223> OTHER INFORMATION: Technical-grade DNA/Residues of polylinker
      sequence
<221> NAME/KEY: misc_feature
<222> LOCATION: (647)..(1398)
<223> OTHER INFORMATION: Part of the 3' region (poxB2) of the poxB gene
<221> NAME/KEY: misc_feature
<222> LOCATION: (1399)..(1454)
<223> OTHER INFORMATION: Technical-grade DNA/Residues of polylinker
      sequence

<400> SEQUENCE: 7
ctagatgcat gctcgagcgg ccgccagtgt gatggatatc tgcagaattc gcccttctga      60
acggtcttag tgacagtctt aatcgcatgg gcaccatcga gtggatgtcc acccgccacg     120
aagaagtggc ggcctttgcc gctggcgctg aagcacaact tagcggagaa ctggcggtct     180
gcgccggatc gtgcggcccc ggcaacctgc acttaatcaa cggcctgttc gattgccacc     240
gcaatcacgt tccggtactg gcgattgccg ctcatattcc ctccagcgaa attggcagcg     300
gctatttcca ggaaacccac ccacaagagc tattccgcga atgtagtcac tattgcgagc     360
tggtttccag cccggagcag atcccacaag tactggcgat tgccatgcgc aaagcggtgc     420
ttaaccgtgg cgtttcggtt gtcgtgttac caggcgacgt ggcgttaaaa cctgcgccag     480
aaggggcaac catgcactgg tatcatgcgc acaaccagt cgtgacgccg aagaagaag       540 agttacgcaa actggcgcaa ctgctgcgtt attccaggcc taagggcgaa ttccagcaca     600
ctggcggccg ttactagtgg atccgagatc tgcagaattc gcccttctgc gtgcattgct     660
tccattggtg gaagaaaaag ccgatcgcaa gtttctggat aaagcgctgg aagattaccg     720
cgacgcccgc aaagggctgg acgatttagc taaaccgagc gagaaagcca ttcacccgca     780
atatctggcg cagcaaatta gtcatttttgc gccgatgac gctattttca cctgtgacgt    840
tggtacgcca acggtgtggg cggcacgtta tctaaaaatg aacggcaagc gtcgcctgtt     900
aggttcgttt aaccacggtt cgatggctaa cgccatgccg caggcgctgg gtgcgcaggc     960
gacagagcca gaacgtcagg tggtcgccat gtgcggcgat ggcggtttta gcatgttgat    1020
gggcgatttc ctctcagtag tgcagatgaa actgccagtg aaaattgtcg tctttaacaa    1080
cagcgtgctg ggcttttgtgg cgatggagat gaaagctggt ggctatttga ctgacggcac    1140
cgaactacac gacacaaact ttgcccgcat tgccgaagcg tgcggcatta cgggtatccg    1200
tgtagaaaaa gcgtctgaag ttgatgaagc cctgcaacgc gccttctcca tcgacggtcc    1260
ggtgttggtg gatgtggtgg tcgccaaaga agagttagcc attccaccgc agatcaaact    1320
cgaacaggcc aaaggtttca gcctgtatat gctgcgcgca atcatcagcg gacgcggtga    1380
tgaagtgatc gaactggcaa gggcgaattc cagcacactg gcggccgtta ctagtggatc    1440
cgagctcggt acca                                                      1454

<210> SEQ ID NO 8
<211> LENGTH: 1448
<212> TYPE: DNA
<213> ORGANISM: Escherichia coli
<220> FEATURE:
<221> NAME/KEY: misc_feature
<222> LOCATION: (1)..(3)
<223> OTHER INFORMATION: Start codon of the delta poxB allele
<221> NAME/KEY: misc_feature
<222> LOCATION: (1)..(605)
<223> OTHER INFORMATION: 5' region of the delta poxB allele
<221> NAME/KEY: misc_feature
```

<222> LOCATION: (606)..(674)
<223> OTHER INFORMATION: Technical-grade DNA/Residues of polylinker
      sequence
<221> NAME/KEY: misc_feature
<222> LOCATION: (675)..(1445)
<223> OTHER INFORMATION: 3' region of the delta poxB allele
<221> NAME/KEY: misc_feature
<222> LOCATION: (1446)..(1448)
<223> OTHER INFORMATION: Stop codon of the delta poxB allele

<400> SEQUENCE: 8

```
atgaaacaaa cggttgcagc ttatatcgcc aaaacactcg aatcggcagg ggtgaaacgc    60
atctggggag tcacaggcga ctctctgaac ggtcttagtg acagtcttaa tcgcatgggc   120
accatcgagt ggatgtccac ccgccacgaa gaagtggcgg cctttgccgc tggcgctgaa   180
gcacaactta gcggagaact ggcggtctgc gccggatcgt gcggccccgg caacctgcac   240
ttaatcaacg gcctgttcga ttgccaccgc aatcacgttc cggtactggc gattgccgct   300
catattccct ccagcgaaat tggcagcggc tatttccagg aaacccaccc acaagagcta   360
ttccgcgaat gtagtcacta ttgcgagctg gtttccagcc cggagcagat cccacaagta   420
ctggcgattg ccatgcgcaa agcggtgctt aaccgtggcg tttcggttgt cgtgttacca   480
ggcgacgtgg cgttaaaacc tgcgccagaa ggggcaacca tgcactggta tcatgcgcca   540
caaccagtcg tgacgccgga agaagaagag ttacgcaaac tggcgcaact gctgcgttat   600
tccaggccta agggcgaatt ccagcacact ggcggccgtt actagtggat ccgagatctg   660
cagaattcgc ccttctgcgt gcattgcttc cattggtgga agaaaaagcc gatcgcaagt   720
ttctggataa agcgctggaa gattaccgcg acgcccgcaa agggctggac gatttagcta   780
aaccgagcga gaaagccatt cacccgcaat atctggcgca gcaaattagt cattttgccg   840
ccgatgacgc tattttcacc tgtgacgttg gtacgccaac ggtgtgggcg gcacgttatc   900
taaaaatgaa cggcaagcgt cgcctgttag gttcgtttaa ccacggttcg atggctaacg   960
ccatgccgca ggcgctgggt gcgcaggcga cagagccaga acgtcaggtg gtcgccatgt  1020
gcggcgatgg cggttttagc atgttgatgg gcgatttcct ctcagtagtg cagatgaaac  1080
tgccagtgaa aattgtcgtc tttaacaaca gcgtgctggg cttttgtggcg atggagatga  1140
aagctggtgg ctatttgact gacggcaccg aactacacga cacaaacttt gcccgcattg  1200
ccgaagcgtg cggcattacg ggtatccgtg tagaaaaagc gtctgaagtt gatgaagccc  1260
tgcaacgcgc cttctccatc gacggtccgg tgttggtgga tgtggtggtc gccaaagaag  1320
agttagccat tccaccgcag atcaaactcg aacaggccaa aggtttcagc ctgtatatgc  1380
tgcgcgcaat catcagcgga cgcggtgatg aagtgatcga actggcgaaa acaaactggc  1440
taaggtaa                                                           1448
```

<210> SEQ ID NO 9
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 9

```
caggacgagg aactaactat g                                              21
```

<210> SEQ ID NO 10
<211> LENGTH: 20
<212> TYPE: DNA
<213> ORGANISM: ARTIFICIAL SEQUENCE

```
<220> FEATURE:
<223> OTHER INFORMATION: SYNTHETIC DNA

<400> SEQUENCE: 10
tcacgatggc ggaatacaac                                              20

<210> SEQ ID NO 11
<211> LENGTH: 2111
<212> TYPE: DNA
<213> ORGANISM: Escherichia coli
<220> FEATURE:
<221> NAME/KEY: RBS
<222> LOCATION: (8)..(12)
<223> OTHER INFORMATION:
<221> NAME/KEY: mutation
<222> LOCATION: (8)..(8)
<223> OTHER INFORMATION: Insertion of the base A at position 8
<221> NAME/KEY: CDS
<222> LOCATION: (19)..(1665)
<223> OTHER INFORMATION:

<400> SEQUENCE: 11
```

| | | | | | | | | | | | | | |
|---|---|---|---|---|---|---|---|---|---|---|---|---|---|
| caggacgagg aactaact | atg | aat | ggc | gca | cag | tgg | gtg | gta | cat | gcg | ttg | | 51 |
| | Met | Asn | Gly | Ala | Gln | Trp | Val | Val | His | Ala | Leu | | |
| | 1 | | | 5 | | | | | 10 | | | | |
| cgg | gca | cag | ggt | gtg | aac | acc | gtt | ttc | ggt | tat | ccg | ggt ggc gca att | 99 |
| Arg | Ala | Gln | Gly | Val | Asn | Thr | Val | Phe | Gly | Tyr | Pro | Gly Gly Ala Ile | |
| | | 15 | | | | 20 | | | | | 25 | | |
| atg | ccg | gtt | tac | gat | gca | ttg | tat | gac | ggc | ggc | gtg | gag cac ttg ctg | 147 |
| Met | Pro | Val | Tyr | Asp | Ala | Leu | Tyr | Asp | Gly | Gly | Val | Glu His Leu Leu | |
| | 30 | | | | 35 | | | | | 40 | | | |
| tgc | cga | cat | gag | cag | ggt | gcg | gca | atg | gcg | gct | atc | ggt tat gcc cgt | 195 |
| Cys | Arg | His | Glu | Gln | Gly | Ala | Ala | Met | Ala | Ala | Ile | Gly Tyr Ala Arg | |
| | 45 | | | | 50 | | | | | 55 | | | |
| gct | acc | ggc | aaa | act | ggc | gta | tgt | atc | gcc | acg | tct | ggt ccg ggc gca | 243 |
| Ala | Thr | Gly | Lys | Thr | Gly | Val | Cys | Ile | Ala | Thr | Ser | Gly Pro Gly Ala | |
| 60 | | | | 65 | | | | | 70 | | | 75 | |
| acc | aac | ctg | ata | acc | ggg | ctt | gcg | gac | gca | ctg | tta | gat tct atc cct | 291 |
| Thr | Asn | Leu | Ile | Thr | Gly | Leu | Ala | Asp | Ala | Leu | Leu | Asp Ser Ile Pro | |
| | | | 80 | | | | | 85 | | | | 90 | |
| gtt | gtt | gcc | atc | acc | ggt | caa | gtg | tcc | gca | ccg | ttt | atc ggc acg gac | 339 |
| Val | Val | Ala | Ile | Thr | Gly | Gln | Val | Ser | Ala | Pro | Phe | Ile Gly Thr Asp | |
| | | 95 | | | | | 100 | | | | | 105 | |
| gca | ttt | cag | gaa | gtg | gat | gtc | ctg | gga | ttg | tcg | tta | gcc tgt acc aag | 387 |
| Ala | Phe | Gln | Glu | Val | Asp | Val | Leu | Gly | Leu | Ser | Leu | Ala Cys Thr Lys | |
| | 110 | | | | 115 | | | | | 120 | | | |
| cac | agc | ttt | ctg | gtg | cag | tcg | ctg | gaa | gag | ttg | ccg | cgc att atg gct | 435 |
| His | Ser | Phe | Leu | Val | Gln | Ser | Leu | Glu | Glu | Leu | Pro | Arg Ile Met Ala | |
| | 125 | | | | 130 | | | | | 135 | | | |
| gaa | gca | ttc | gac | gtt | gcc | agc | tca | ggt | cgt | cct | ggt | ccg gtt ctg gtc | 483 |
| Glu | Ala | Phe | Asp | Val | Ala | Ser | Ser | Gly | Arg | Pro | Gly | Pro Val Leu Val | |
| 140 | | | | 145 | | | | | 150 | | | 155 | |
| gat | atc | cca | aaa | gat | atc | cag | cta | gcc | agc | ggt | gac | ctg gaa ccg tgg | 531 |
| Asp | Ile | Pro | Lys | Asp | Ile | Gln | Leu | Ala | Ser | Gly | Asp | Leu Glu Pro Trp | |
| | | | 160 | | | | | 165 | | | | 170 | |
| ttc | acc | acc | gtt | gaa | aac | gaa | gtg | act | ttc | cca | cat | gcc gaa gtt gag | 579 |
| Phe | Thr | Thr | Val | Glu | Asn | Glu | Val | Thr | Phe | Pro | His | Ala Glu Val Glu | |
| | | 175 | | | | | 180 | | | | | 185 | |
| caa | gcg | cgc | cag | atg | ctg | gca | aaa | gcg | caa | aaa | ccg | atg ctg tac gtt | 627 |
| Gln | Ala | Arg | Gln | Met | Leu | Ala | Lys | Ala | Gln | Lys | Pro | Met Leu Tyr Val | |
| | 190 | | | | 195 | | | | | 200 | | | |
| ggt | ggt | ggc | gtg | ggt | atg | gcg | cag | gca | gtt | cct | gct | tta cga gaa ttt | 675 |
| Gly | Gly | Gly | Val | Gly | Met | Ala | Gln | Ala | Val | Pro | Ala | Leu Arg Glu Phe | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 205 |     |     |     | 210 |     |     |     |     | 215 |     |     |     |     |     |      |
| ctc | gct | acc | aca | aaa | atg | cct | gcc | acc | tgc | acg | ctg | aaa | ggg | ctg | ggc | 723  |
| Leu | Ala | Thr | Thr | Lys | Met | Pro | Ala | Thr | Cys | Thr | Leu | Lys | Gly | Leu | Gly |      |
| 220 |     |     |     | 225 |     |     |     |     | 230 |     |     |     |     | 235 |     |      |
| gca | gtt | gaa | gca | gat | tat | ccg | tac | tat | ctg | ggc | atg | ctg | gga | atg | cat | 771  |
| Ala | Val | Glu | Ala | Asp | Tyr | Pro | Tyr | Tyr | Leu | Gly | Met | Leu | Gly | Met | His |      |
|     |     |     |     | 240 |     |     |     |     | 245 |     |     |     |     | 250 |     |      |
| ggc | acc | aaa | gcg | gcg | aac | ttc | gcg | gtg | cag | gag | tgc | gac | ttg | ctg | atc | 819  |
| Gly | Thr | Lys | Ala | Ala | Asn | Phe | Ala | Val | Gln | Glu | Cys | Asp | Leu | Leu | Ile |      |
|     |     |     | 255 |     |     |     |     | 260 |     |     |     |     | 265 |     |     |      |
| gcc | gtg | ggt | gca | cgt | ttt | gat | gac | cgg | gtg | acc | ggc | aaa | ctg | aac | acc | 867  |
| Ala | Val | Gly | Ala | Arg | Phe | Asp | Asp | Arg | Val | Thr | Gly | Lys | Leu | Asn | Thr |      |
|     |     | 270 |     |     |     |     | 275 |     |     |     |     | 280 |     |     |     |      |
| ttc | gca | cca | cac | gcc | agt | gtt | atc | cat | atg | gat | atc | gac | ccg | gca | gaa | 915  |
| Phe | Ala | Pro | His | Ala | Ser | Val | Ile | His | Met | Asp | Ile | Asp | Pro | Ala | Glu |      |
|     | 285 |     |     |     |     | 290 |     |     |     |     | 295 |     |     |     |     |      |
| atg | aac | aag | ctg | cgt | cag | gca | cat | gtg | gca | tta | caa | ggt | gat | tta | aat | 963  |
| Met | Asn | Lys | Leu | Arg | Gln | Ala | His | Val | Ala | Leu | Gln | Gly | Asp | Leu | Asn |      |
| 300 |     |     |     |     | 305 |     |     |     |     | 310 |     |     |     |     | 315 |      |
| gct | ctg | tta | cca | gca | tta | cag | cag | ccg | tta | aat | atc | aat | gac | tgg | cag | 1011 |
| Ala | Leu | Leu | Pro | Ala | Leu | Gln | Gln | Pro | Leu | Asn | Ile | Asn | Asp | Trp | Gln |      |
|     |     |     |     | 320 |     |     |     |     | 325 |     |     |     |     | 330 |     |      |
| cta | cac | tgc | gcg | cag | ctg | cgt | gat | gaa | cat | gcc | tgg | cgt | tac | gac | cat | 1059 |
| Leu | His | Cys | Ala | Gln | Leu | Arg | Asp | Glu | His | Ala | Trp | Arg | Tyr | Asp | His |      |
|     |     |     | 335 |     |     |     |     | 340 |     |     |     |     | 345 |     |     |      |
| ccc | ggt | gac | gct | atc | tac | gcg | cca | ttg | ttg | tta | aaa | caa | ctg | tcg | gat | 1107 |
| Pro | Gly | Asp | Ala | Ile | Tyr | Ala | Pro | Leu | Leu | Leu | Lys | Gln | Leu | Ser | Asp |      |
|     |     | 350 |     |     |     |     | 355 |     |     |     |     | 360 |     |     |     |      |
| cgt | aaa | cct | gcg | gat | tgc | gtc | gtg | acc | aca | gat | gtg | ggg | cag | cac | cag | 1155 |
| Arg | Lys | Pro | Ala | Asp | Cys | Val | Val | Thr | Thr | Asp | Val | Gly | Gln | His | Gln |      |
|     | 365 |     |     |     |     | 370 |     |     |     |     | 375 |     |     |     |     |      |
| atg | tgg | gcc | gcg | cag | cac | atc | gca | cac | act | cgc | ccg | gaa | aat | ttc | att | 1203 |
| Met | Trp | Ala | Ala | Gln | His | Ile | Ala | His | Thr | Arg | Pro | Glu | Asn | Phe | Ile |      |
| 380 |     |     |     |     | 385 |     |     |     |     | 390 |     |     |     |     | 395 |      |
| acc | tcc | agc | ggc | tta | ggc | acc | atg | ggt | ttc | ggt | tta | cca | gcg | gcg | gtt | 1251 |
| Thr | Ser | Ser | Gly | Leu | Gly | Thr | Met | Gly | Phe | Gly | Leu | Pro | Ala | Ala | Val |      |
|     |     |     |     | 400 |     |     |     |     | 405 |     |     |     |     | 410 |     |      |
| ggc | gca | caa | gtc | gca | cga | ccg | aac | gat | act | gtc | gtc | tgt | atc | tcc | ggt | 1299 |
| Gly | Ala | Gln | Val | Ala | Arg | Pro | Asn | Asp | Thr | Val | Val | Cys | Ile | Ser | Gly |      |
|     |     |     | 415 |     |     |     |     | 420 |     |     |     |     | 425 |     |     |      |
| gac | ggc | tct | ttc | atg | atg | aat | gtg | caa | gag | ctg | ggc | acc | gta | aaa | cgc | 1347 |
| Asp | Gly | Ser | Phe | Met | Met | Asn | Val | Gln | Glu | Leu | Gly | Thr | Val | Lys | Arg |      |
|     |     | 430 |     |     |     |     | 435 |     |     |     |     | 440 |     |     |     |      |
| aag | cag | tta | ccg | ttg | aaa | atc | gtc | tta | ctc | gat | aac | caa | cgg | tta | ggg | 1395 |
| Lys | Gln | Leu | Pro | Leu | Lys | Ile | Val | Leu | Leu | Asp | Asn | Gln | Arg | Leu | Gly |      |
|     | 445 |     |     |     |     | 450 |     |     |     |     | 455 |     |     |     |     |      |
| atg | gtt | cga | caa | tgg | cag | caa | ctg | ttt | ttt | cag | gaa | cga | tac | agc | gaa | 1443 |
| Met | Val | Arg | Gln | Trp | Gln | Gln | Leu | Phe | Phe | Gln | Glu | Arg | Tyr | Ser | Glu |      |
| 460 |     |     |     |     | 465 |     |     |     |     | 470 |     |     |     |     | 475 |      |
| acc | acc | ctt | act | gat | aac | ccc | gat | ttc | ctc | atg | tta | gcc | agc | gcc | ttc | 1491 |
| Thr | Thr | Leu | Thr | Asp | Asn | Pro | Asp | Phe | Leu | Met | Leu | Ala | Ser | Ala | Phe |      |
|     |     |     |     | 480 |     |     |     |     | 485 |     |     |     |     | 490 |     |      |
| ggc | atc | cct | ggc | caa | cac | atc | acc | cgt | aaa | gac | cag | gtt | gaa | gcg | gca | 1539 |
| Gly | Ile | Pro | Gly | Gln | His | Ile | Thr | Arg | Lys | Asp | Gln | Val | Glu | Ala | Ala |      |
|     |     |     | 495 |     |     |     |     | 500 |     |     |     |     | 505 |     |     |      |
| ctc | gac | acc | atg | ctg | aac | agt | gat | ggg | cca | tac | ctg | ctt | cat | gtc | tca | 1587 |
| Leu | Asp | Thr | Met | Leu | Asn | Ser | Asp | Gly | Pro | Tyr | Leu | Leu | His | Val | Ser |      |
|     |     | 510 |     |     |     |     | 515 |     |     |     |     | 520 |     |     |     |      |
| atc | gac | gaa | ctt | gag | aac | gtc | tgg | ccg | ctg | gtg | ccg | cct | ggc | gcc | agt | 1635 |

```
Ile Asp Glu Leu Glu Asn Val Trp Pro Leu Val Pro Pro Gly Ala Ser
            525                 530                 535 aat tca gaa atg ttg gag aaa tta tca tga tgcaacatca ggtcaatgta      1685
Asn Ser Glu Met Leu Glu Lys Leu Ser
540                 545 tcggctcgct tcaatccgga aaccttagaa cgtgttttac gcgtggtgcg tcatcgtggt   1745
ttccacgtct gctcaatgaa tatggctgcc gccagcgatg cacaaaatat aaatatcgaa   1805
ttgaccgttg ccagcccacg gtcggtcgac ttactgttta gtcagttaaa taaactggtg   1865
gacgtcgcac acgttgccat ctgccagagc acaaccacat cacaacaaat ccgcgcctga   1925
gcgcaaaagg aatataaaaa tgaccacgaa gaaagctgat tacatttggt tcaatgggga   1985
gatggttcgc tgggaagacg cgaaggtgca tgtgatgtcg cacgcgctgc actatggcac   2045
ctcggttttt gaaggcatcc gttgctacga ctcacacaaa ggaccggttg tattccgcca   2105
tcgtga                                                              2111

<210> SEQ ID NO 12
<211> LENGTH: 548
<212> TYPE: PRT
<213> ORGANISM: Escherichia coli

<400> SEQUENCE: 12

Met Asn Gly Ala Gln Trp Val Val His Ala Leu Arg Ala Gln Gly Val
1               5                   10                  15

Asn Thr Val Phe Gly Tyr Pro Gly Gly Ala Ile Met Pro Val Tyr Asp
            20                  25                  30

Ala Leu Tyr Asp Gly Gly Val Glu His Leu Leu Cys Arg His Glu Gln
        35                  40                  45

Gly Ala Ala Met Ala Ala Ile Gly Tyr Ala Arg Ala Thr Gly Lys Thr
    50                  55                  60

Gly Val Cys Ile Ala Thr Ser Gly Pro Gly Ala Thr Asn Leu Ile Thr
65                  70                  75                  80

Gly Leu Ala Asp Ala Leu Leu Asp Ser Ile Pro Val Val Ala Ile Thr
                85                  90                  95

Gly Gln Val Ser Ala Pro Phe Ile Gly Thr Asp Ala Phe Gln Glu Val
            100                 105                 110

Asp Val Leu Gly Leu Ser Leu Ala Cys Thr Lys His Ser Phe Leu Val
        115                 120                 125

Gln Ser Leu Glu Glu Leu Pro Arg Ile Met Ala Glu Ala Phe Asp Val
    130                 135                 140

Ala Ser Ser Gly Arg Pro Gly Pro Val Leu Val Asp Ile Pro Lys Asp
145                 150                 155                 160

Ile Gln Leu Ala Ser Gly Asp Leu Glu Pro Trp Phe Thr Thr Val Glu
                165                 170                 175

Asn Glu Val Thr Phe Pro His Ala Glu Val Glu Gln Ala Arg Gln Met
            180                 185                 190

Leu Ala Lys Ala Gln Lys Pro Met Leu Tyr Val Gly Gly Gly Val Gly
        195                 200                 205

Met Ala Gln Ala Val Pro Ala Leu Arg Glu Phe Leu Ala Thr Thr Lys
    210                 215                 220

Met Pro Ala Thr Cys Thr Leu Lys Gly Leu Gly Ala Val Glu Ala Asp
225                 230                 235                 240

Tyr Pro Tyr Tyr Leu Gly Met Leu Gly Met His Gly Thr Lys Ala Ala
                245                 250                 255
```

```
Asn Phe Ala Val Gln Glu Cys Asp Leu Leu Ile Ala Val Gly Ala Arg
                260                 265                 270

Phe Asp Asp Arg Val Thr Gly Lys Leu Asn Thr Phe Ala Pro His Ala
            275                 280                 285

Ser Val Ile His Met Asp Ile Asp Pro Ala Glu Met Asn Lys Leu Arg
        290                 295                 300

Gln Ala His Val Ala Leu Gln Gly Asp Leu Asn Ala Leu Leu Pro Ala
305                 310                 315                 320

Leu Gln Gln Pro Leu Asn Ile Asn Asp Trp Gln Leu His Cys Ala Gln
                325                 330                 335

Leu Arg Asp Glu His Ala Trp Arg Tyr Asp His Pro Gly Asp Ala Ile
            340                 345                 350

Tyr Ala Pro Leu Leu Lys Gln Leu Ser Asp Arg Lys Pro Ala Asp
        355                 360                 365

Cys Val Val Thr Thr Asp Val Gly Gln His Gln Met Trp Ala Ala Gln
        370                 375                 380

His Ile Ala His Thr Arg Pro Glu Asn Phe Ile Thr Ser Ser Gly Leu
385                 390                 395                 400

Gly Thr Met Gly Phe Gly Leu Pro Ala Ala Val Gly Ala Gln Val Ala
                405                 410                 415

Arg Pro Asn Asp Thr Val Val Cys Ile Ser Gly Asp Gly Ser Phe Met
            420                 425                 430

Met Asn Val Gln Glu Leu Gly Thr Val Lys Arg Lys Gln Leu Pro Leu
        435                 440                 445

Lys Ile Val Leu Leu Asp Asn Gln Arg Leu Gly Met Val Arg Gln Trp
450                 455                 460

Gln Gln Leu Phe Phe Gln Glu Arg Tyr Ser Glu Thr Thr Leu Thr Asp
465                 470                 475                 480

Asn Pro Asp Phe Leu Met Leu Ala Ser Ala Phe Gly Ile Pro Gly Gln
                485                 490                 495

His Ile Thr Arg Lys Asp Gln Val Glu Ala Ala Leu Asp Thr Met Leu
            500                 505                 510

Asn Ser Asp Gly Pro Tyr Leu Leu His Val Ser Ile Asp Glu Leu Glu
        515                 520                 525

Asn Val Trp Pro Leu Val Pro Pro Gly Ala Ser Asn Ser Glu Met Leu
    530                 535                 540

Glu Lys Leu Ser
545

<210> SEQ ID NO 13
<211> LENGTH: 2111
<212> TYPE: DNA
<213> ORGANISM: Escherichia coli
<220> FEATURE:
<221> NAME/KEY: RBS
<222> LOCATION: (8)..(12)
<223> OTHER INFORMATION:
<221> NAME/KEY: mutation
<222> LOCATION: (8)..(8)
<223> OTHER INFORMATION: Insertion of the base A at position 8
<221> NAME/KEY: CDS
<222> LOCATION: (1662)..(1925)
<223> OTHER INFORMATION:

<400> SEQUENCE: 13
caggacgagg aactaactat gaatggcgca cagtgggtgg tacatgcgtt gcgggcacag      60
ggtgtgaaca ccgttttcgg ttatccgggt ggcgcaatta tgccggttta cgatgcattg     120
```

-continued

```
tatgacggcg gcgtggagca cttgctgtgc cgacatgagc agggtgcggc aatggcggct      180
atcggttatg cccgtgctac cggcaaaact ggcgtatgta tcgccacgtc tggtccgggc      240
gcaaccaacc tgataaccgg gcttgcggac gcactgttag attctatccc tgttgttgcc      300
atcaccggtc aagtgtccgc accgtttatc ggcacggacg catttcagga agtggatgtc      360 ctggattgt cgttagcctg taccaagcac agctttctgg tgcagtcgct ggaagagttg       420
ccgcgcatta tggctgaagc attcgacgtt gccagctcag gtcgtcctgg tccggttctg      480
gtcgatatcc caaagatat ccagctagcc agcggtgacc tggaaccgtg gttcaccacc       540
gttgaaaacg aagtgacttt cccacatgcc gaagttgagc aagcgcgcca gatgctggca      600
aaagcgcaaa aaccgatgct gtacgttggt ggtggcgtgg gtatggcgca ggcagttcct     660
gctttacgag aatttctcgc taccacaaaa atgcctgcca cctgcacgct gaaagggctg      720
ggcgcagttg aagcagatta tccgtactat ctgggcatgc tgggaatgca tggcaccaaa     780
gcggcgaact tcgcggtgca ggagtgcgac ttgctgatcg ccgtgggtgc acgttttgat      840
gaccgggtga ccgcaaaact gaacaccttc gcaccacacg ccagtgttat ccatatggat     900
atcgacccgg cagaaatgaa caagctgcgt caggcacatg tggcattaca aggtgattta      960
aatgctctgt taccagcatt acagcagccg ttaaatatca atgactgca gctacactgc      1020 gcgcagctgc gtgatgaaca tgcctggcgt tacgaccatc ccggtgacgc tatctacgcg     1080
ccattgttgt taaacaact gtcggatcgt aaacctgcgg attgcgtcgt gaccacagat      1140
gtggggcagc accagatgtg ggccgcgcag cacatcgcac acactcgccc ggaaaatttc     1200
attacctcca gcggcttagg caccatgggt ttcggtttac cagcggcggt tggcgcacaa     1260
gtcgcacgac cgaacgatac tgtcgtctgt atctccggtg acggctcttt catgatgaat     1320
gtgcaagagc tgggcaccgt aaaacgcaag cagttaccgt tgaaaatcgt cttactcgat     1380
aaccaacggt tagggatggt tcgacaatgg cagcaactgt tttttcagga acgatacagc     1440
gaaaccaccc ttactgataa ccccgatttc ctcatgttag ccagcgcctt cggcatccct     1500
ggccaacaca tcacccgtaa agaccaggtt gaagcggcac tcgacaccat gctgaacagt     1560
gatgggccat acctgcttca tgtctcaatc gacgaacttg agaacgtctg ccgctggtg      1620 ccgcctggcg ccagtaattc agaaatgttg gagaaattat c atg atg caa cat cag     1676
                                              Met Met Gln His Gln
                                                1           5 gtc aat gta tcg gct cgc ttc aat ccg gaa acc tta gaa cgt gtt tta        1724
Val Asn Val Ser Ala Arg Phe Asn Pro Glu Thr Leu Glu Arg Val Leu
         10              15                  20 cgc gtg gtg cgt cat cgt ggt ttc cac gtc tgc tca atg aat atg gct       1772
Arg Val Val Arg His Arg Gly Phe His Val Cys Ser Met Asn Met Ala
     25                  30                  35 gcc gcc agc gat gca caa aat ata aat atc gaa ttg acc gtt gcc agc      1820
Ala Ala Ser Asp Ala Gln Asn Ile Asn Ile Glu Leu Thr Val Ala Ser
         40              45                  50 cca cgg tcg gtc gac tta ctg ttt agt cag tta aat aaa ctg gtg gac      1868
Pro Arg Ser Val Asp Leu Leu Phe Ser Gln Leu Asn Lys Leu Val Asp
 55                  60                  65 gtc gca cac gtt gcc atc tgc cag agc aca acc aca tca caa caa atc      1916
Val Ala His Val Ala Ile Cys Gln Ser Thr Thr Thr Ser Gln Gln Ile
 70              75                  80                  85 cgc gcc tga gcgcaaaagg aatataaaaa tgaccacgaa gaaagctgat                1965
Arg Ala tacatttggt tcaatgggga gatggttcgc tgggaagacg cgaaggtgca tgtgatgtcg     2025
```

-continued

```
cacgcgctgc actatggcac ctcggttttt gaaggcatcc gttgctacga ctcacacaaa    2085
ggaccggttg tattccgcca tcgtga                                          2111
```

<210> SEQ ID NO 14
<211> LENGTH: 87
<212> TYPE: PRT
<213> ORGANISM: Escherichia coli

<400> SEQUENCE: 14

```
Met Met Gln His Gln Val Asn Val Ser Ala Arg Phe Asn Pro Glu Thr
1               5                   10                  15

Leu Glu Arg Val Leu Arg Val Val Arg His Arg Gly Phe His Val Cys
                20                  25                  30

Ser Met Asn Met Ala Ala Ala Ser Asp Ala Gln Asn Ile Asn Ile Glu
            35                  40                  45

Leu Thr Val Ala Ser Pro Arg Ser Val Asp Leu Leu Phe Ser Gln Leu
        50                  55                  60

Asn Lys Leu Val Asp Val Ala His Val Ala Ile Cys Gln Ser Thr Thr
65                  70                  75                  80

Thr Ser Gln Gln Ile Arg Ala
                85
```

PROCESS FOR PREPARATION OF D-PANTOTHENIC ACID AND/OR SALTS THEREOF

This application claims the benefit of priority to provisional application 60/304,776 filed Jul. 13, 2001.

BACKGROUND OF THE INVENTION

1. Field of the Invention

This invention relates to a process for the preparation of D-pantothenic acid and/or a salt thereof using a microorganism of the Enterobacteriaceae family in which at least the poxB gene is attenuated.

2. Discussion of the Background

Pantothenic acid is produced worldwide in an order of magnitude of several thousand tons a year. It is used, inter alia, in human medicine, in the pharmaceuticals industry and in the foodstuffs industry. A large portion of the pantothenic acid produced is used for nutrition of stock animals such as poultry and pigs.

Pantothenic acid can be prepared by chemical synthesis, or biotechnologically by fermentation of suitable microorganisms in suitable nutrient solutions. In the chemical synthesis, DL-pantolactone is an important precursor. It is prepared in a multi-stage process from formaldehyde, isobutylaldehyde and cyanide. In further process steps, the racemic mixture is separated, D-pantolactone is subjected to a condensation reaction with β-alanine, and D-pantothenic acid is obtained.

The typical commercial form is the calcium salt of D-pantothenic acid. The calcium salt of the racemic mixture of D,L-pantothenic acid is also customary.

The advantage of the fermentative preparation by microorganisms lies in the direct formation of the desired stereoisomeric D-form, which is free from L-pantothenic acid.

Various types of bacteria, such as Escherichia coli (E. coli), Arthrobacter ureafaciens, Corynebacterium erythrogenes, Brevibacterium ammoniagenes, and also yeasts, such as Debaromyces castellii, can produce D-pantothenic acid in a nutrient solution which comprises glucose, DL-pantoic acid and β-alanine, as shown in EP-A 0 493 060. This patent furthermore shows that in the case of E. coli the formation of D-pantothenic acid is improved by amplification of pantothenic acid biosynthesis genes from E. coli which are contained on the plasmids pFV3 and pFV5 in a nutrient solution comprising glucose, DL-pantoic acid and β-alanine.

EP-A 0 590 857 and U.S. Pat. No. 5,518,906 describe mutants derived from E. coli strain IF03547, such as FV5714, FV525, FV814, FV521, FV221, FV6051 and FV5069, which carry resistances to various antimetabolites, such as salicylic acid, α-ketobutyric acid, β-hydroxyaspartic acid, o-methylthreonine and α-ketoisovaleric acid. They produce pantoic acid in a nutrient solution comprising glucose, and D-pantothenic acid in a nutrient solution comprising glucose and β-alanine. It is furthermore stated in EP-A 0 590 857 and U.S. Pat. No. 5,518,906 that after amplification of the pantothenic acid biosynthesis genes panB, panC and panD, which are said to be contained on the plasmid pFV31, in the above-mentioned strains the production of D-pantoic acid in nutrient solutions comprising glucose and the production of D-pantothenic acid in a nutrient solution comprising glucose and β-alanine is improved.

The favorable effect of enhancement of the ilvGM operon on production of D-pantothenic acid is furthermore reported in WO97/10340. Finally, the effect of enhancement of the panE gene on the formation of D-pantothenic acid is reported in EP-A-1001027.

According to the prior art, D-pantothenic acid or the corresponding salt is isolated from the fermentation broth and purified (EP-A-0590857 and WO96/33283) and accordingly used in purified form, or the fermentation broth comprising D-pantothenic acid is dried in total (EP-A-1050219) and used in particular as a feedstuffs additive.

SUMMARY OF THE INVENTION

It is an object of the present invention to provide a novel method for the preparation of D-pantothenic acid and/or a salt thereof.

It is another object of the present invention to provide an animal feedstuffs additive comprising D-pantothenic acid and/or its salt.

These and other objects have been achieved by the present invention the first embodiment which includes a process for the preparation of D-pantothenic acid and/or a salt thereof comprising:

preparing D-pantothenic acid and/or a salt thereof by fermentation of a microorganism of the Enterobacteriaceae family in which at least a nucleotide sequence which codes for a poxB gene is attenuated, thereby attenuating an intracellular activity of pyruvate oxidase.

DETAILED DESCRIPTION OF THE INVENTION

Figure 1:
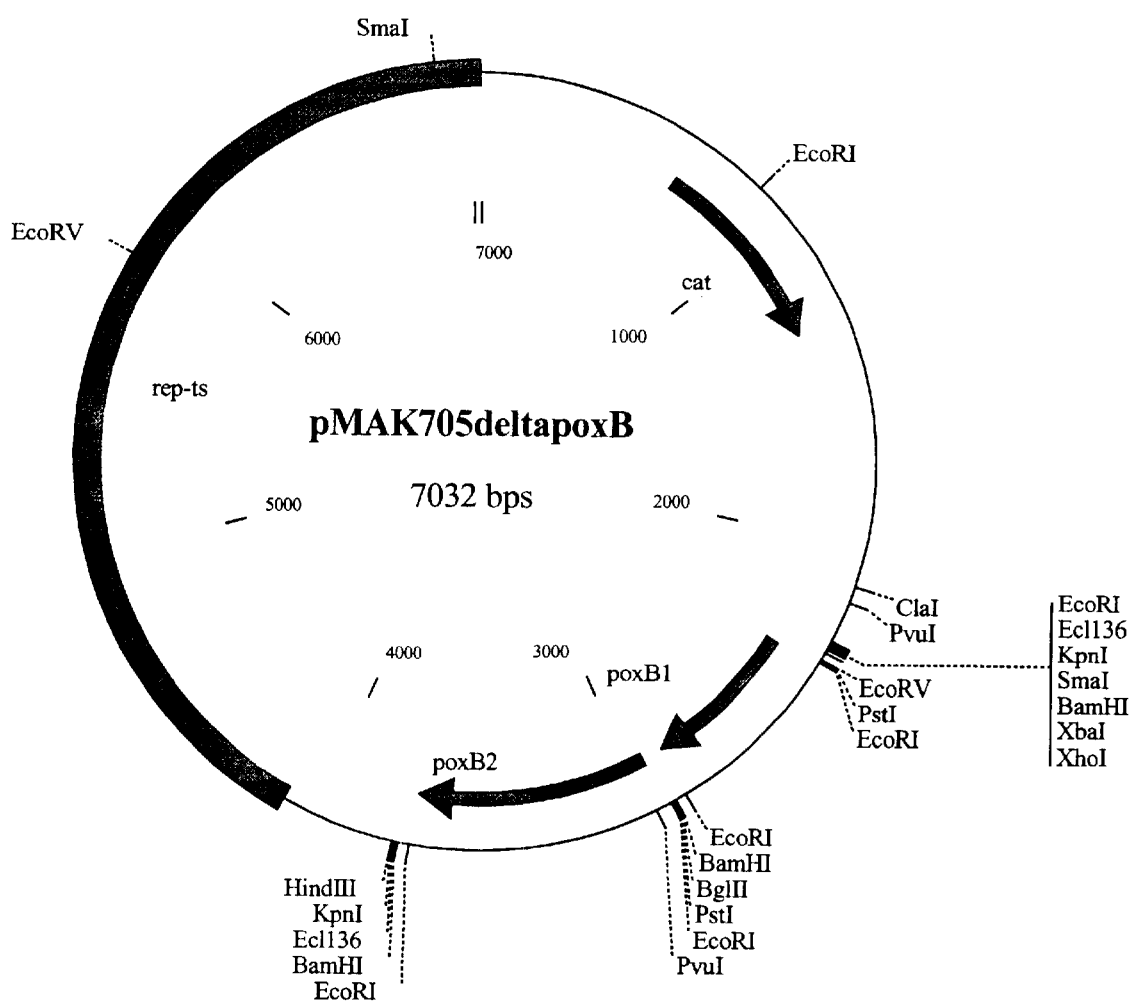
FIG. 1 shows the vector pMAK705ΔpoxB (=pMAK705deltapoxB).

In the context of the present invention, the term "D-pantothenic acid" or "pantothenic acid" include not only the free acids but also the salts of D-pantothenic acid, such as e.g. the calcium, sodium, ammonium or potassium salt.

The invention provides a process for the preparation of D-pantothenic acid and/or salts thereof using microorganisms of the Enterobacteriaceae family which preferably already produce D-pantothenic acid and in which the nucleotide sequence(s) which code(s) for the poxB gene are attenuated, preferably eliminated.

Preferably, the following steps are carried out in the process of the present invention:

a) fermentation of a microorganism of the Enterobacteriaceae family in which at least the poxB gene is attenuated or switched off, optionally in combination with attenuation or enhancement of at least one other gene;

b) optionally in the presence of an alkaline earth metal compound which is added continuously or discontinuously in preferably stoichiometric amounts;

c) concentration of the D-pantothenic acid or of the corresponding salt in the medium or the fermentation broth or in the cells of the microorganism of the Enterobacteriaceae family; and d) after conclusion of the fermentation, isolation of the D-pantothenic acid, and/or of the corresponding salt.

The invention also provides a process in which, after conclusion of the fermentation, the biomass remains in the fermentation broth in an amount of ≧0 to 100%. The amount of biomass includes all values and subvalues therebetween, especially including 0.5, 1, 5, 10, 20, 30, 40, 50, 60, 70, 80 and 90%. The obtained broth is processed, optionally after concentration, to a solid mixture which comprises D-pantothenic acid and/or salts thereof. The solid mixture further comprises conventional constituents of the fermentation broth (in an amount of >0 to 100%), provided these are formed or added. The amount of conventional constituents includes all values and subvalues therebetween, especially including 0.5, 1, 5, 10, 20, 30, 40, 50, 60, 70, 80 and 90%.

The term "attenuation" in the context of the present invention describes the reduction or elimination of the intracellular activity of one or more enzymes (proteins) in a microorganism which are coded by the corresponding DNA, for example, by using a weak promoter or using a gene or allele which codes for a corresponding enzyme (protein) with a low activity or inactivates the corresponding gene or enzyme (protein), and optionally combining these measures.

By attenuation measures, the enzymatic activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism. The activity or concentration of the protein after attenuation includes all values and subvalues therebetween, especially including 5, 10, 15, 20, 25, 30, 35, 40, 45, 50, 55, 60, 65 and 70%.

The microorganisms of the present invention can produce D-pantothenic acid from glucose, sucrose, lactose, fructose, maltose, molasses, starch, cellulose or from glycerol and ethanol. They are representatives of Enterobacteriaceae, preferably of the genus Escherichia. Particularly preferred is the species *Escherichia coli*. Within the species *Escherichia coli* the so-called K-12 strains are preferred, such as the strains MG1655 or W3110 (Neidhard et al.: *Escherichia coli* and Salmonella. Cellular and Molecular Biology (ASM Press, Washington D.C.)) or the *Escherichia coli* wild type strain IFO3547 (Institute of Fermentation, Osaka, Japan) and mutants derived from these which have the ability to produce D-pantothenic acid.

Preferred D-pantothenic acid-producing strains of the genus Escherichia, in particular of the species *Escherichia coli*, are, for example

*Escherichia coli*, FV5069/pFV31,

*Escherichia coli* FV5069/pFV202,

*Escherichia coli* FE6/pFE80, and

*Escherichia coli* KE3.

The inventors of the present invention have found that Enterobacteriaceae produce D-pantothenic acid in an improved manner after attenuation of the poxB gene, which codes for pyruvate oxidase (EC 1.2.2.2.).

The nucleotide sequence of the poxB gene of *Escherichia coli* has been published by Grabau and Cronan (Nucleic Acids Research. 14 (13), 5449–5460 (1986)) and can also be found from the genome sequence of *Escherichia coli* published by Blattner et al. (Science 277, 1453–1462 (1997), under Accession Number AE000188.

The poxB genes described in the above references mentioned can be used according to the invention. Alleles of the poxB gene which result from the degeneracy of the genetic code or due to sense mutations of neutral function can be furthermore used.

To achieve an attenuation, for example, expression of the poxB gene or the catalytic properties of the enzyme protein can be reduced or eliminated. The two measures can be optionally combined.

The reduction in gene expression can take place by suitable culturing, by genetic modification (mutation) of the signal structures of gene expression, or by the antisense-RNA technique. Signal structures of gene expression are, for example, repressor genes, activator genes, operators, promoters, attenuators, ribosome binding sites, the start codon and terminators. The expert can find information in this respect, inter alia, for example, in Jensen and Hammer (Biotechnology and Bioengineering 58: 191–195 (1998)), in Carrier and Keasling (Biotechnology Progress 15, 58–64 (1999), in Franch and Gerdes (Current Opinion in Microbiology 3, 159–164 (2000)) and in known textbooks of genetics and molecular biology, such as, for example, the textbook of Knippers ("Molekulare Genetik [Molecular Genetics]", 6th edition, Georg Thieme Verlag, Stuttgart, Germany, 1995) or that of Winnacker ("Gene und Klone [Genes and Clones]", VCH Verlagsgesellschaft, Weinheim, Germany, 1990).

Mutations which lead to a change or reduction in the catalytic properties of enzyme proteins are known. Examples are the works of Qiu and Goodman (Journal of Biological Chemistry 272: 8611–8617 (1997)), Yano et al. (Proceedings of the National Academy of Sciences, USA 95, 5511–5515 (1998), Wente and Schachmann (Journal of Biological Chemistry 266, 20833–20839 (1991). Summarizing descriptions can be found in known textbooks of genetics and molecular biology, such as e.g. that by Hagemann ("Allgemeine Genetik [General Genetics]", Gustav Fischer Verlag, Stuttgart, 1986).

Possible mutations are transitions, transversions, insertions and deletions. Depending on the effect of the amino acid exchange on the enzyme activity, "missense mutations" or "nonsense mutations" are referred to. Insertions or deletions of at least one base pair in a gene lead to "frame shift mutations", which lead to incorrect amino acids being incorporated or translation being interrupted prematurely. Deletions of several codons typically lead to a complete loss of the enzyme activity. Instructions on generation of such mutations can be found in known textbooks of genetics and molecular biology, such as e.g. the textbook by Knippers ("Molekulare Genetik [Molecular Genetics]", 6th edition, Georg Thieme Verlag, Stuttgart, Germany, 1995), the textbook by Winnacker ("Gene und Klone [Genes and Clones]", VCH Verlagsgesellschaft, Weinheim, Germany, 1990) or the textbook by Hagemann ("Allgemeine Genetik [General Genetics]", Gustav Fischer Verlag, Stuttgart, 1986).

Suitable mutations in the poxB gene, such as, for example, deletion mutations, can be incorporated into suitable strains by gene or allele replacement.

A conventional method is the method, described by Hamilton et al. (Journal of Bacteriology 174, 4617–4622 (1989)), of gene replacement with the aid of a conditionally replicating pSC101 derivative pMAK705. Other methods have been described, such as, for example, in Martinez-Morales et al. (Journal of Bacteriology 1999, 7143–7148 (1999)) or in Boyd et al. (Journal of Bacteriology 182, 842–847 (2000)). They can likewise be used.

It is also possible to transfer mutations in the poxB gene or mutations which affect expression of the poxB gene into various strains by conjugation or transduction.

It is furthermore preferred for the production of D-pantothenic acid with strains of the Enterobacteriaceae family, in addition to the attenuation of the poxB gene, for one or more preferably endogenous genes to be enhanced and more preferably to be over-expressed. These endogenous genes are preferably selected from the group consisting of the ilvGM operon which codes for acetohydroxy-acid synthase II (WO 97/10340), the panB gene which codes for ketopantoate hydroxymethyl transferase (U.S. Pat. No. 5,518,906), the panE gene which codes for ketopantoate reductase (EP-A-1001027), the panD gene which codes for aspartate decarboxylase (U.S. Pat. No. 5,518,906), the panC gene which codes for pantothenate synthetase (U.S. Pat. No. 5,518,906), the serC gene which codes for phosphoserine transaminase (Duncan and Coggins, Biochemical Journal 234:49–57 (1986)), the gcvT, gcvH and gcvP genes which code for the glycine cleavage system, (Okamura-Ikeda et al., European Journal of Biochemistry 216, 539–548 (1993)), and the glyA gene which codes for serine hydroxymethyl transferase (Plamann et al Nucleic Acids Research 11(7):2065–2075(1983)).

The term "enhancement" in the context of the present invention describes the increase in the intracellular activity of one or more enzymes or proteins in a microorganism which are coded by the corresponding DNA, for example by increasing the number of copies of the gene or genes, using a potent promoter or a gene or allele which codes for a corresponding enzyme or protein with a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism. The activity or concentration of the corresponding protein after enhancement includes all values and subvalues therebetween, especially including 100, 200, 300, 400, 500, 600, 700, 800, 900, 1000, 1100, 1200, 1300, 1400, 1500, 1600, 1700, 1800 and 1900%.

The incorporation of a mutation which causes resistance to L-valine (J. H. Miller, A Short Course in Bacterial Genetics, A Laboratory Manual and Handbook for *Escherichia coli* and Related Bacteria Cold Spring Harbor Laboratory Press, USA, 1992) into microorganisms of the Enterobacteriaceae family which produce pantothenic acid is also favorable for pantothenic acid production.

Finally, it is preferred for the production of D-pantothenic acid with strains of the Enterobacteriaceae family, to have further genes in addition to the attenuation of the poxB gene, preferably endogenous genes to be attenuated, particularly preferably eliminated or at least expressed as a low level, such as, for example the avtA gene which codes for transaminase C (EP-A-1001027), and the pckA gene which codes for PEP carboxykinase (Medina et al., Journal of Bacteriology 172, 7151–7156 (1990)).

In addition to the attenuation of the poxB gene it is furthermore preferred for the production of D-pantothenic acid to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982). Bacteria in which the metabolic pathways which reduce the formation of D-pantothenic acid are at least partly eliminated can be employed in the process according to the invention.

The microorganisms produced according to the present invention can be cultured in the batch process (batch culture), the fed batch (feed process) or the repeated fed batch process (repetitive feed process). A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substance can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Precursors of pantothenic acid, such as aspartate, β-alanine, ketoisovalerate, ketopantoic acid or pantoic acid and optionally salts thereof, can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture.

For the preparation of alkaline earth metal salts of pantothenic acid, in particular the calcium salt, it is equally possible to add the suspension or solution of a) an inorganic compound containing an alkaline earth metal, such as, for example, calcium hydroxide, or of b) an organic compound, such as the alkaline earth metal salt of an organic acid, for example calcium acetate, continuously or discontinuously during the fermentation. In this manner, the cation necessary for preparation of the desired alkaline earth metal salt of D-pantothenic acid is introduced into the fermentation broth directly in the desired amount, preferably in stoichiometric amounts.

Antifoams, such as e.g. fatty acid polyglycol esters, can be employed to control the development of foam. Suitable substances having a selective action, e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 25° C. to 45° C., and preferably 30° C. to 40° C. The temperature includes all values and subvalues therebetween, especially including 27, 29, 31, 33, 35, 37, 39, 41 and 43° C. Culturing is continued until a maximum of D-pantothenic acid has formed. This target is usually reached within 10 hours to 160 hours. The culturing time includes all values and subvalues therebetween, especially including 20, 30, 40, 50, 60, 70, 80, 90, 100, 110, 120, 130, 140 and 150 hours.

The D-pantothenic acid or the corresponding salts of D-pantothenic acid contained in the fermentation broth can then be isolated and purified according to known methods.

It is also possible for the fermentation broths comprising D-pantothenic acid and/or salts thereof preferably first to be freed from all or some of the biomass by known separation methods, such as, for example, centrifugation, filtration, decanting or a combination thereof. However, it is also possible to leave the biomass in its entirety in the fermentation broth. In general, the suspension or solution is preferably concentrated and worked up to a powder, for example, with the aid of a spray dryer or a freeze-drying unit. This powder is then in general converted by suitable compacting or granulating processes, for example, build-up granulation, into a coarser-grained, free-flowing, storable and largely dust-free product with the desired particle size distribution of 20 to 2000 μm, in particular 100 to 1400 μm. The particle size includes all values and subvalues therebetween, especially including 50, 100, 200, 300, 400, 500, 600, 700, 800, 900, 1000, 1100, 1200, 1300, 1400, 1500, 1600, 1700, 1800 and 1900 μm.

In the conversion of the fermentation broth and its constituents into the solid phase it is advantageous to employ conventional organic or inorganic auxiliary substances or carriers, such as starch, gelatin, cellulose derivatives or similar substances, such as those which are conventionally used as binders, gelling agents or thickeners in foodstuffs or feedstuffs processing, or further substances, such as, for example, silicas, silicates or stearates.

Alternatively, the fermentation product, with or without further conventional fermentation constituents, can be absorbed onto an organic or inorganic carrier substance which is known and conventional in feedstuffs processing, such as, for example, silicas, silicates, grits, brans, meals, starches, sugars or others, and/or stabilized with conventional thickeners or binders. Examples and processes in this context are described in the literature (Die Mühle+Mischfuttertechnik 132 (1995) 49, page 817).

D-Pantothenic acid and/or the desired salt of D-pantothenic acid or a formulation comprising these compounds is optionally added at a suitable process stage in order to achieve or establish the desired content of pantothenic acid and/or the desired salt in the end product.

The desired total content of pantothenic acid and/or salt thereof is in general in the range from 20 to 80 wt. % (dry weight). The total content of pantothenic acid and/or salt thereof includes all values and subvalues therebetween, especially including 25, 30, 35, 40, 45, 50, 55, 60, 65, 70 and 75% (dry weight).

The concentration of pantothenic acid can be determined with known chemical methods (Velisek; Chromatographic Science 60, 515–560 (1992)) or microbiological methods, such as e.g. the Lactobacillus plantarum test (DIFCO MANUAL, 10th Edition, p. 1100–1102; Michigan, USA).

A pure culture of the *Escherichia coli* K-12 strain DH5α/pMAK705 was deposited as DSM 13720 on Sep. 12, 2000, at the Deutsche Sammlung für Mikroorganismen und Zellkulturen (DSMZ=German Collection of Microorganisms and Cell Cultures, Braunschweig, Germany) in accordance with the Budapest Treaty.

A pure culture of the *Escherichia coli* K-12 strain MG44ΔpoxB was deposited as DSM 13762 on Oct. 2, 2000, at the Deutsche Sammlung für Mikroorganismen und Zellkulturen (DSMZ=German Collection of Microorganisms and Cell Cultures, Braunschweig, Germany) in accordance with the Budapest Treaty.

Having generally described this invention, a further understanding can be obtained by reference to certain specific examples which are provided herein for purposes of illustration only, and are not intended to be limiting unless otherwise specified.

EXAMPLES

The isolation of plasmid DNA from *Escherichia coli* and all techniques of restriction, Klenow and alkaline phosphatase treatment were carried out according to the method of Sambrook et al. (Molecular cloning—A laboratory manual (1989) Cold Spring Harbor Laboratory Press). Unless described otherwise, the transformation of *Escherichia coli* was carried out according to the method of Chung et al. (Proceedings of the National Academy of Sciences of the United States of America USA (1989) 86: 2172–2175).

The incubation temperature for the preparation of strains and transformants was 37° C. Temperatures of 30° C. and 44° C. were used in the gene replacement method of Hamilton et. al.

Example 1

Construction of the Deletion Mutation of the poxB Gene

Parts of the 5' and 3' region of the poxB gene were amplified from *Escherichia coli* K12 using the polymerase chain reaction (PCR) and synthetic oligonucleotides. Starting from the nucleotide sequence of the poxB gene in *E. coli* K12 MG1655 (SEQ ID No. 1), the following PCR primers were synthesized (MWG Biotech, Ebersberg, Germany):

```
                                           (SEQ ID NO: 3)
poxB'5'-1:  5' -CTGAACGGTCTTAGTGACAG-3'

(SEQ ID NO: 4)
poxB'5'-2:  5' -AGGCCTGGAATAACGCAGCAGTTG-3'

(SEQ ID NO: 5)
poxB'3'-1:  5' -CTGCGTGCATTGCTTCCATTG-3'

(SEQ ID NO: 5)
poxB'3'-2:  5' -GCCAGTTCGATCACTTCATCAC-3'
```

The chromosomal *E. coli* K12 MG1655 DNA employed for the PCR was isolated according to the manufacturers instructions with "Qiagen Genomic-tips 100/G" (QIAGEN, Hilden, Germany). A DNA fragment approx. 500 base pairs (bp) in size from the 5' region of the poxB gene (called poxB1) and a DNA fragment approx. 750 bp in size from the 3' region of the poxB gene (called poxB2) was amplified with the specific primers under standard PCR conditions (Innis et al. (1990) PCR Protocols. A Guide to Methods and Applications, Academic Press) with Taq-DNA polymerase (Gibco-BRL, Eggenstein, Germany). The PCR products were each ligated with the vector pCR2.1TOPO (TOPO TA Cloning Kit, Invitrogen, Groningen, The Netherlands) in accordance with the manufacturers instructions and transformed into the *E. coli* strain TOP10F'.

Selection of plasmid-carrying cells took place on LB agar, to which 50 μg/ml ampicillin were added. After isolation of the plasmid DNA, the vector pCR2.1TOPOpoxB1 was cleaved with the restriction enzymes Ecl136II and XbaI (Restriction endonuclease from *Xanthomonas badrii*) and, after separation in 0.8% agarose gel, the poxB1 fragment was isolated with the aid of the QIAquick Gel Extraction Kit (QIAGEN, Hilden, Germany). After isolation of the plasmid DNA the vector pCR2.1TOPOpoxB2 was cleaved with the enzymes EcoRV (Restriction endonuclease from *Escherichia coli*) and XbaI and ligated with the poxB1 fragment isolated. The *E. coli* strain DH5α was transformed with the ligation batch and plasmid-carrying cells were selected on LB agar, to which 50 µg/ml ampicillin was added. After isolation of the plasmid DNA those plasmid in which the mutagenic DNA sequence shown in SEQ ID No. 7 is cloned were detected by control cleavage with the enzymes SpeI and XbaI. One of the plasmids is called pCR2.1TOPΔpoxB.

Example 2

Construction of the Replacement Vector pMAK705ΔpoxB

The poxB allele described in Example 1 was isolated from the vector pCR2.1TOPΔpoxB after restriction with the enzymes HindIII (Restriction endonuclease from *Haemophilus influenzae*) and XbaI and separation in 0.8% agarose gel, and ligated with the plasmid pMAK705 (Hamilton et al. (1989) Journal of Bacteriology 174, 4617–4622), which had been digested with the enzymes HindIII and XbaI. The ligation batch was transformed in DH5Δ and plasmid-carrying cells were selected on LB agar, to which 20 µg/ml chloramphenicol were added. Successful cloning was demonstrated after isolation of the plasmid DNA and cleavage with the enzymes HindIII and XbaI. The replacement vector formed, pMAK705ΔpoxB (=pMAK705deltapoxB), is shown in FIG. 1.

Example 3

Position-specific Mutagenesis of the poxB Gene in the *E. coli* Strain MG442

The L-threonine-producing *E. coli* strain MG442 is described in the patent specification U.S. Pat. No. 4,278,765 and deposited as CMIM B-1628 at the Russian National Collection for Industrial Microorganisms (VKPM, Moscow, Russia).

For replacement of the chromosomal poxB gene with the plasmid-coded deletion construct, MG442 was transformed with the plasmid pMAK705DpoxB. The gene replacement was carried out by the selection method described by Hamilton et al. (1989) Journal of Bacteriology 174, 4617–4622) and was verified by standard PCR methods (Innis et al. (1990) PCR Protocols. A Guide to Methods and Applications, Academic Press) with the following oligonucleotide primers:

(SEQ ID NO: 3)
poxB'5'-1: 5' -CTGAACGGTCTTAGTGACAG-3'

(SEQ ID NO: 6)
poxB'3'-1: 5' -GCCAGTTCGATCACTTCATCAC-3'

After replacement had taken place, MG442 contained the form of the ΔpoxB allele shown in SEQ ID No. 8. The strain obtained is called MG442ΔpoxB.

Example 4

Preparation of D-Pantothenic Acid With the Strain MG442ΔpoxB/pFV31ilvGM 4.1 Amplification and Cloning of the ilvGM Gene The ilvGM operon from *Escherichia coli* IFO3547 which codes for acetohydroxy acid synthase II (Institut für Fermentation [Institute of Fermentation], Osaka, Japan) was amplified using the polymerase chain reaction (PCR) and synthetic oligonucleotides. Starting from the nucleotide sequence of the ilvGM operon in *E. coli* K12 MG1655 (GenBank: Accession No. M87049), PCR primers were synthesized, (MWG Biotech, Ebersberg, Germany). The sequence of the primer ilvGM1 was chosen such that it contains an adenine at position 8. As a result, a modified ribosome binding site was generated 7 nucleotides upstream of the start codon of the ilvG protein (Coding region of the large subunit of acetohydroxy acid synthase II).

(SEQ ID NO: 9)
IlvGM1'5'-1: 5' -CAGGACGAGGAACTAACTATG-3'

(SEQ ID NO: 10)
IlvGM2'5'-1: 5' -TCACGATGGCGGAATACAAC-3'

The chromosomal *E. coli* IFO3547 DNA employed for the PCR was isolated according to the manufacturers instructions with "QIAGEN Genomic-tips 100/G" (QIAGEN, Hilden, Germany). A DNA fragment approx. 2100 bp in size, which comprises the modified ribosome binding site, the ilvGM coding regions and approx. 180 bp 3'-flanking sequences, was amplified with the specific primers under standard PCR conditions (Innis et al.: PCR protocols. A guide to methods and applications, 1990, Academic Press) with Pfu-DNA polymerase (Promega Corporation, Madison, USA). The PCR product was cloned in the plasmid pCR-BluntII-TOPO and transformed in the *E. coli* strain TOP10 (Invitrogen, Groningen, The Netherlands, Product Description Zero Blunt TOPO PCR Cloning Kit, Cat. No. K2800-20). Successful cloning was demonstrated by cleavage of the plasmid pCR-BluntIFO3547ilvGM with the restriction enzymes EcoRI (Restriction endonuclease from *Escherichia coli*) and SphI (Restriction nuclease from *Streptomyces phaeochromogenes*). For this, the plasmid DNA was isolated by means of the "QIAprep Spin Plasmid Kit" (QIAGEN, Hilden, Germany) and, after cleavage, separated in a 0.8% agarose gel. The DNA sequence of the amplified fragment was determined using the reverse and universal sequencing primer (QIAGEN, Hilden, Germany). The sequence of the PCR product is shown in SEQ ID No. 11 and 13. The ilvG gene or allele is identified in SEQ ID No. 11. The ilvM (Coding region of the small subunit of acetohydroxy acid synthase II) gene or allele is identified in SEQ ID No. 13. The associated gene products or proteins are shown in SEQ ID No. 12 and 14.

4.2 Cloning of the ilvGM Gene in the Expression Vector pTrc99A

Figure 2:
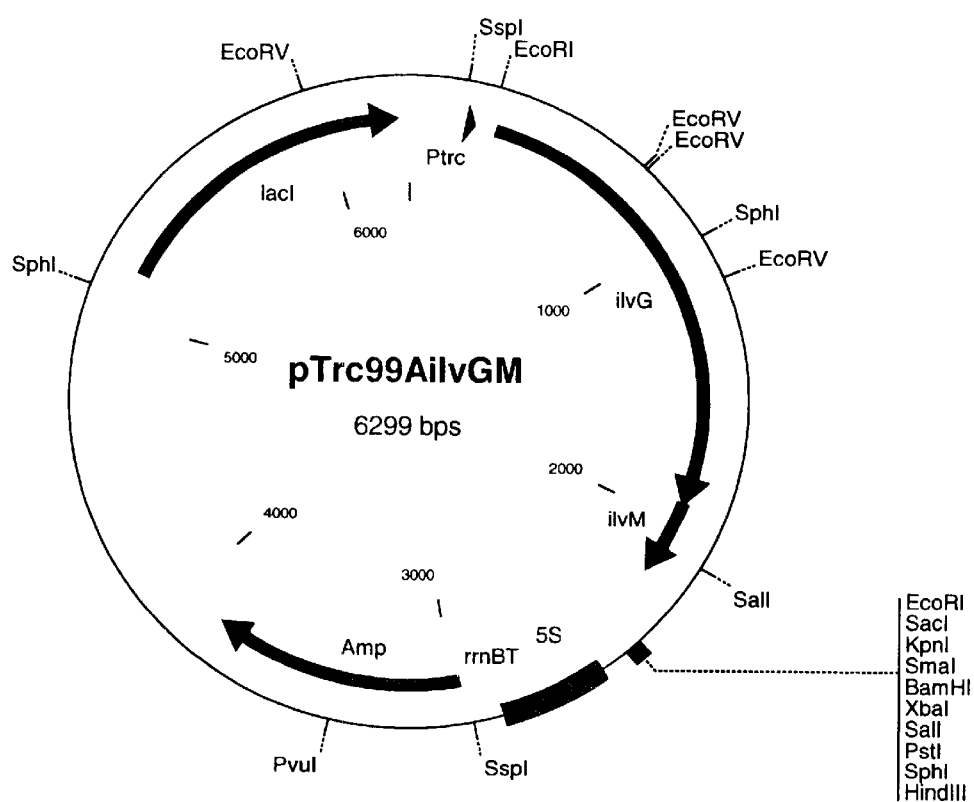
FIG. 2 shows the vector pTrc99AilvGM.

The ilvGM genes described in Example 4.1 were cloned in the vector pTrc99A (Amersham Pharmacia Biotech Inc, Uppsala, Sweden) for expression in *Escherichia coli* K12. For this, the plasmid pCR-BluntIFO3547ilvGM was cleaved with the enzyme EcoRI, the cleavage batch was separated in 0.8% agarose gel and the ilvGM fragment 2.1 kbp in size was isolated with the aid of the QIAquick Gel Extraction Kit (QIAGEN, Hilden, Germany). The vector pTrc99A was cleaved with the enzyme EcoRI, an alkaline phosphatase treatment was carried out, and ligation was carried out with the ilvGM fragment isolated. The ligation batch was transformed in the E. coli strain DH5α. Selection of pTrc99A-carrying cells was carried out on LB agar (Lennox, Virology 1:190 (1955)), to which 50 μg/ml ampicillin was added. Successful cloning of the ilvGM operon was demonstrated after plasmid DNA isolation and control cleavage with SalI (Restriction endonuclease from *Streptomyces albus*) and SphI. In the vector, which is called pTrc99AilvGM (FIG. 2), expression of the ilvGM operon is regulated by the Ptrc promoter (trc promoter region, IPTG-inducible) lying upstream of the modified ribosome binding site and by the rRNA terminator region lying downstream of the ilvGM coding region.

4.3 Construction of the Vector pFV31ilvGM

Figure 3:
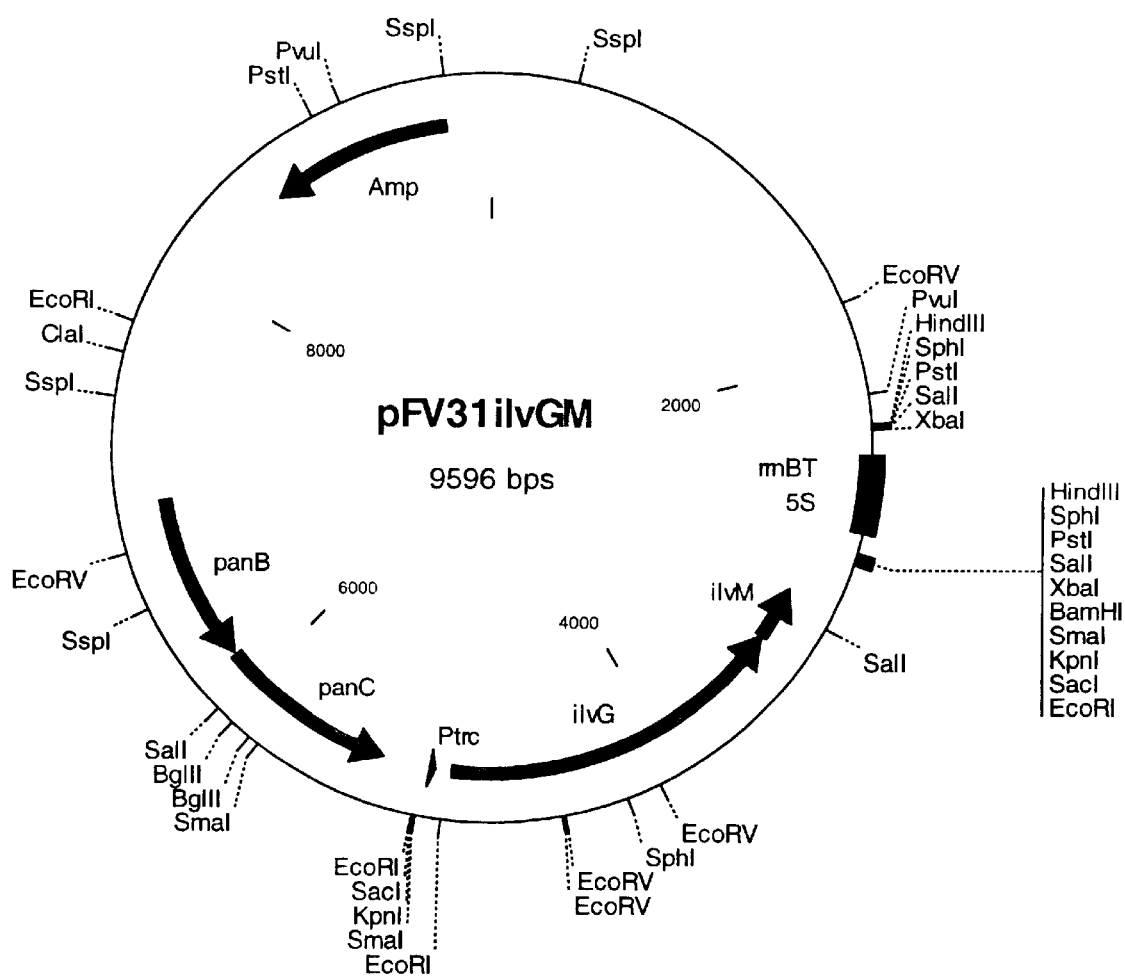
FIG. 3 shows the vector pFV31ilvGM.

The E. coli strain FV5069/pFV31 which produces D-pantothenic acid is described in EP-A-0590857 and deposited as FERM BP 4395 in accordance with the Budapest Treaty. The plasmid pFV31 was isolated from FV5069/pFV31, cleaved with the enzyme BamHI (Restriction endonuclease from *Bacillus amyloliquefaciens*), and the projecting 3' ends were treated with Klenow enzyme. An alkaline phosphatase treatment was then carried out. From the vector pTrc99AilvGM described in Example 4.2, after restriction with the enzyme SspI (Restriction endonuclease from Sphaerotilus species) and separation of the cleavage batch in 0.8% agarose gel, the ilvGM expression cassette 2.8 kbp in size was isolated and ligated with the linearized and dephosphorylated vector pFV31. The ligation batch was transformed in the E. coli strain DH5α and plasmid-carrying cells were selected on LB agar, to which 50 μg/ml ampicillin were added. Successful cloning of the ilvGM expression cassette was demonstrated after plasmid DNA isolation and control cleavage with HindIII, SalI, SmaI (Restriction endonuclease from *Serratia marcescens*), SphI and XbaI. The plasmid is called pFV31ilvGM (FIG. 3).

4.4 Preparation of the Strain MG442DpckA/pFV31ilvGM

The strain MG442DpoxB obtained in Example 3 and the strain MG442 were transformed with the plasmid pFV31ilvGM and transformants were selected on LB agar, which was supplemented with 50 μg/ml ampicillin. The strains MG442DpoxB/pFV31ilvGM and MG442/pFV31ilvGM were formed in this manner.

4.5 Preparation of D-Pantothenic Acid With the Strain MG442ΔpoxB/pFV31ilvGM

The pantothenate production of the E. coli strains MG442/pFV31ilvGM and MG442ΔpoxB/pFV31ilvGM was checked in batch cultures of 10 ml contained in 100 ml conical flasks. For this, 10 ml of preculture medium of the following composition: 2 g/l yeast extract, 10 g/l (NH$_4$)$_2$SO$_4$, 1 g/l KH$_2$PO$_4$, 0.5 g/l MgSO$_4$*7H$_2$O, 15 g/l CaCO$_3$, 20/l glucose, 50 μg/ml ampicillin, were inoculated with an individual colony and incubated for 20 hours at 33° C. and 200 rpm on an ESR incubator from Kühner AG (Birsfelden, Switzerland). In each case 200 μl of this preculture were transinoculated into 10 ml of production medium (25 g/l (NH$_4$)$_2$SO$_4$, 2 g/l KH$_2$PO$_4$, 1 g/l MgSO$_4$*7H$_2$O, 0.03 g/l FeSO$_4$*7H$_2$O, 0.018 g/l MnSO$_4$*1H$_2$O, 30 g/l CaCO$_3$, 20 g/l glucose, 20 g/l β-alanine, 250 mg/l thiamine) and the batch was incubated for 48 hours at 37° C. and 200 rpm. After the incubation the optical density (OD) of the culture suspension was determined with an LP2W photometer from Dr. Lange (Düsseldorf, Germany) at a measurement wavelength of 660 nm.

The concentration of D-pantothenate formed in the sterile-filtered culture supernatant was then determined by means of the Lactobacillus plantarum ATCC8014 pantothenate assay in accordance with the instructions of DIFCO (DIFCO MANUAL, 10th Edition, p. 1100–1102; Michigan, USA). D(+)-Pantothenic acid calcium salt hydrate (catalogue number 25,972-1, Sigma-Aldrich, Deisenhofen, Germany) was used for the calibration.

The result of the experiment is shown in Table 1.

TABLE 1

| Strain | OD (660 nm) | Pantothenate g/l |
|---|---|---|
| MG442/pFV31ilvGM | 2.7 | 1.35 |
| MG442ΔpoxB/pFV31ilvGM | 3.5 | 1.76 |

The length data are to be understood as approx. data.

German patent application 101 12 102.4, filed Mar. 14, 2001, and provisional U.S. patent application No. 60/304,776, filed Jul. 13, 2001, are incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A process for the preparation of D-pantothenic acid and/or a salt thereof, comprising: eliminating an intracellular activity of a pyruvate oxidase enzyme comprising the amino acid sequence of SEQ ID NO: 2 encoded by the poxB gene of a microorganism of the genus Escherichia; and fermenting said microorganism; wherein elimination is achieved by one or more methods selected from the group consisting of a) deletion mutagenesis with deletion of at least one base pair in said poxB gene, b) insertional mutagenesis due to homologus recombination, and c) transition or trasversion mutagenesis with incorporation of a nonsense mutation in said poxB gene.

2. The process according to claim 1, wherein at least the nucleotide sequence which codes for the poxB gene is eliminated.

3. The process according to claim 1, wherein
   a) the D-pantothenic acid and/or the salt thereof is concentrated in a fermentation broth or in the cells of the microorganism, and
   b) after the end of the fermentation, the D-pantothenic acid and/or the salt thereof is isolated and the biomass and/or a further constituent of the fermentation broth are separated off in an amount of ≧0 to 100%.

4. The process according to claim 1, wherein the fermentation is carried out in the presence of an alkaline earth metal salt which is added continuously or discontinuously, and wherein a product comprising an alkaline earth metal salt of D-pantothenic acid is obtained.

5. The process according to claim 4, wherein a stoichiometric amount of the alkaline earth metal salt is added.

6. The process according to claim 1, wherein the microorganism originates from the species Escherichia coli.

7. The process according to claim 1, wherein said microorganism is a bacterium which has a resistance to L-valine.

8. The process according to claim 1, wherein the expression of a polynucleotide which encloses the pyruvate oxidase enzyme which is attenuated.

9. The process according to claim 1, wherein the expression of a polynucleotide which encloses the pyruvate oxidase enzyme is eliminated.

* * * * *